United States Patent [19]

Alfano et al.

[11] Patent Number: 5,625,458
[45] Date of Patent: Apr. 29, 1997

[54] METHOD AND SYSTEM FOR IMAGING OBJECTS IN TURBID MEDIA USING DIFFUSIVE FERMAT PHOTONS

[75] Inventors: Robert R. Alfano, Bronx; Alexander Y. Polishchuk, Brooklyn, both of N.Y.

[73] Assignee: Research Foundation of City College of New York, New York, N.Y.

[21] Appl. No.: 384,112

[22] Filed: Feb. 3, 1995

Related U.S. Application Data

[63] Continuation-in-part of Ser. No. 338,019, Nov. 10, 1994, abandoned.

[51] Int. Cl.$^6$ .................. A61B 5/00; A61B 6/00
[52] U.S. Cl. .................. 356/446; 178/633; 178/664; 178/665
[58] Field of Search .................. 356/332–343, 356/446; 250/341.1, 358.1, 341.8; 178/673, 664–665

[56] References Cited

U.S. PATENT DOCUMENTS

| | | | |
|---|---|---|---|
| 4,515,165 | 5/1985 | Carroll | 128/664 |
| 5,140,463 | 8/1992 | Yoo et al. | 356/337 |
| 5,142,372 | 8/1992 | Alfano et al. | 358/209 |
| 5,203,339 | 4/1993 | Knuttel et al. | 128/665 |
| 5,227,912 | 7/1993 | Ho et al. | 359/258 |
| 5,275,168 | 1/1994 | Reinjes et al. | 128/665 |
| 5,299,035 | 3/1994 | Leith et al. | 359/9 |
| 5,349,951 | 9/1994 | Ito et al. | 128/665 |
| 5,353,799 | 10/1994 | Chance | 138/665 |
| 5,369,496 | 11/1994 | Alfano et al. | 356/445 |
| 5,371,368 | 12/1994 | Alfano et al. | 128/664 |
| 5,416,582 | 5/1995 | Knutson et al. | 128/665 |
| 5,418,797 | 5/1995 | Bashkansky et al. | 128/665 |

OTHER PUBLICATIONS

Alfano et al., "Photons for prompt tumor detection," Physics World, pp. 37–40 (Jan. 1992).

Feynman et al., "Quantum Mechanics and Path Integrals," pp. 336–340, McGraw-Hill Book Company, New York (1965).

Yoo et al., "Time–resolved coherent and incoherent components of forward light scattering in random media," Optics Letters, 15(6):320–2 (Mar. 15, 1990).

(List continued on next page.)

*Primary Examiner*—Frank Gonzalez
*Assistant Examiner*—Jason D. Eisenberg
*Attorney, Agent, or Firm*—Kriegsman & Kriegsman

[57] ABSTRACT

A method for imaging objects in turbid media. According to one embodiment of the invention, the method comprises the steps of (a) illuminating the object through the turbid medium with a pulse of light, the light emergent from the turbid medium consisting of a ballistic component, a snake-like component and a diffusive component, the diffusive component including Fermat photons and non-Fermat photons; (b) gating the light emergent from the turbid medium to preferentially select Fermat photons; and (c) forming an image of the object using the gated light. Preferably, a spatial gate is used to preferentially select Fermat photons from the emergent light. This may be done by orienting the source of the illuminating light and a light detector to lie along a most favorable path travelled predominately by Fermat photons. A time gate, such as a streak camera or the like, may be used in addition to the spatial gate to more carefully select Fermat photons from the emergent light. The above-described method may also be used to produce a tomography map of a turbid medium for use in detecting an object located within the turbid medium. This may be done, for example, by providing two or more pairs of light sources and light detectors which are arranged to provide intersecting most favorable paths. The present invention is also directed to systems constructed in accordance with the foregoing methods.

26 Claims, 9 Drawing Sheets

OPTICAL TOMOGRAPHY

OTHER PUBLICATIONS

Wang et al., "Ballistic 2-D Imaging Through Scattering Walls Using an Ultrafast Optical Kerr Gate," Science, 253:769–71 (Aug. 16, 1991).

Feng et al., "Monte Carlo Simulations of Photon Migration Path Distributions in Multiple Scattering Media," SPIE, 1888:78–89 (1993).

Perelman et al., "Photon Migration in Turbid Media Using Path Integrals," Physical Review Letters, 72(9):1341–4 (Feb. 28, 1994).

O'Leary et al., "Refractin of Diffuse Photon Density Waves," Physical Review Letters, 69(18):2658–61 (Nov. 2, 1992).

Yoo et al., "When Does the Diffusion Approximation Fail to Descirbe Photon Transport in Random Media," Physical Review Letters, 64(22):2647–50 (May 28, 1990).

Chen et al., "Two-dimensional imaging through diffusing media using 150-fs gated electronics holography techniques," Optics Letters, 16(7):487–9 (Apr. 1, 1991).

Hee et al., "Femtosecond transillumination tomography in thick tissues," Optics Letters, 18(13):1107–9 (Jul. 1, 1993).

Duncan et al., "Time-gated imaging through scattering media using stimulated Raman amplification," Optics Letters, 16(23):1868–70 (Dec. 1, 1991).

METHOD AND SYSTEM FOR IMAGING OBJECTS IN TURBID MEDIA USING DIFFUSIVE FERMAT PHOTONS

CROSS-REFERENCE TO RELATED APPLICATIONS

The present application is a continuation-in-part of presently pending U.S. patent application Ser. No. 08/338,019, filed Nov. 10, 1994, now abandoned.

BACKGROUND OF THE INVENTION

The present invention relates generally to the imaging of objects in turbid media and more particularly to a novel technique for imaging objects in turbid media.

As can readily be appreciated, there are many situations in which the detection of an object present in a turbid, i.e., highly scattering, medium is highly desirable. For instance, the detection of a tumor embedded within a tissue is one such example. Although X-ray techniques do provide some measure of success in detecting objects in turbid media, they are not well-suited for detecting very small objects, e.g., tumors less than 1 mm in size, or for detecting objects in thick media. In addition, X-ray radiation can present safety hazards to a person exposed thereto.

An alternative technique used to detect objects in turbid media is transillumination. In transillumination, visible light is incident on one side of a medium and the light emergent from the opposite side of the medium is used to form an image. Objects embedded in the medium typically absorb the incident light and appear in the image as shadows. Unfortunately, the usefulness of transillumination as a detection technique is severely limited in those instances in which the medium is thick or the object is very small. This is because light scattering within the medium contributes to noise and reduces the intensity of the unscattered light used to form the image shadow.

To improve the detectability of small objects located in a turbid medium using transillumination, many investigators have attempted to selectively use only certain components of the transilluminating light signal. This may be done by exploiting the properties of photon migration through a scattering medium. Photons migrating through a turbid medium have traditionally been categorized into three major signal components: (1) the ballistic (coherent) photons which arrive first by traveling over the shortest, most direct path; (2) the snake (quasi-coherent) photons which arrive within the first δt after the ballistic photons and which deviate, only to a very slight extent, off a straight-line propagation path; and (3) the diffusive (incoherent) photons which experience comparatively more scattering than do ballistic and snake photons and, therefore, deviate more considerably from the straight-line propagation path followed by ballistic and snake photons.

Because it has been believed that ballistic and snake photons contain the least distorted image information and that diffusive photons lose most of the image information, efforts to make transillumination work most effectively with turbid media have focused on techniques which permit the selective detection of ballistic and snake photons while rejecting diffusive photons. This process of selection and rejection have been implemented in various time-gating, space-gating and time/space-gating techniques. Patents, patent applications and publications which disclose certain of these techniques include U.S. Pat. No. 5,140,463, inventors Yoo et al., which issued Aug. 18, 1992; U.S. Pat. No. 5,142,372, inventors Alfano et al., which issued Aug. 25, 1992; U.S. Pat. No. 5,227,912, inventors Ho et al., which issued Jul. 13, 1993; U.S. Pat. No. 5,371,368, inventors Alfano et al., filed Jul. 23, 1992; Alfano et al., "Photons for prompt tumor detection," *Physics World*, pp. 37–40 (January 1992); Wang et al., "Ballistic 2-D Imaging Through Scattering Walls Using an Ultrafast Optical Kerr Gate," *Science*, Vol. 253, pp. 769–771 (Aug. 16, 1991); Wang et al., "Kerr-Fourier imaging of hidden objects in thick turbid media," *Optics Letters*, Vol. 18, No. 3, pp. 241–243 (Feb. 1, 1993); Yoo et al., "Time-resolved coherent and incoherent components of forward light scattering in random media," *Optics Letter*, Vol. 15, No. 6, pp. 320–322 (Mar. 15, 1990); Chen et al., "Two-dimensional imaging through diffusing media using 150-fs gated electronic holography techniques," *Optics Letters*, Vol. 16, No. 7, pp. 487–489 (Apr. 1, 1991); Duncan et al., "Time-gated imaging through scattering media using stimulated Raman amplification," *Optics Letters*, Vol. 16, No. 23, pp. 1868–1870 (Dec. 1, 1991), all of which are incorporated herein by reference.

Of the above-listed art, Wang et al., "Kerr-Fourier imaging of hidden objects in thick turbid media," *Optics Letters*, Vol. 18, No. 3, pp. 241–243 (Feb. 1, 1993) is illustrative. In this article, there is disclosed a time/space-gating system for use in imaging opaque test bars hidden inside a 5.5 cm-thick 2.5% Intralipid solution. The disclosed system includes three main parts: a laser source, an optical Kerr gate and a detector. The laser source is a picosecond mode-locked laser system, which emits a 1054 nm, 8 ps laser pulse train as the illumination source. The second harmonic of the pulse train, which is generated by transmission through a potassium dihydrate phosphate (KDP) crystal, is used as the gating source. The illumination source is sent through a variable time-delay and is then used to transilluminate, from one side, the turbid medium containing the opaque object. The signal from the turbid medium located at the front focal plane of a lens is collected and transformed to a Kerr cell located at its back focal plane (i.e., the Fourier-transform spectral plane of a 4F system). That portion of the Kerr cell located at the focal point of the 4F system is gated at the appropriate time using the gating source so that only the ballistic and snake components are permitted to pass therethrough. The spatial-filtered and temporal-segmented signal is then imaged by a second lens onto a CCD camera.

Although techniques of the type described above, which selectively use ballistic and snake photons to image objects in turbid media, have enjoyed a modicum of success, such techniques have been limited by the fact that detected light signals derived from ballistic and snake photons are typically rather weak, due to the proportionately small number of transilluminated ballistic and snake photons. This problem is further exacerbated in those instances in which the turbid medium is thick and the likelihood of substantial scattering increases.

An experimental imaging scheme using diffusive light requires a theoretical algorithm to restore the internal properties of an object from the array of measured experimental data. The necessity for using mathematical methods is evoked by the fact that measured quantities are merely integral characteristics of the object properties and that the diffusive photons have lost their potential for shadowgram since they travel over the medium in random ways. The diffusive photons wander over the medium in a tortuous manner. These photons sample various parts of the medium, some never entering the defect.

Over the years, there have been several efforts to use diffusive light to image inside and map the internal structure of an object. These efforts depend on how one inverts the experimental scattering data obtained around the object to give information on the various points in the medium using some inverse algorithm and reconstruction approach. The equation used mainly depends on the diffusion equation, higher approximation or just the probability of the random walk given by the Monte Carlo method. Since the photons wander about, this problem is ill posed. There are many attempts at solving the problem and the path undergone. There are a number of models based on the diffusion approximation (e.g., M. Patterson et al., *SPIE*, 1767, 372 (1992); J. Schotland et al., *App. Opt.*, 32, 448 (1993)). Though the latter uses the concept of photon paths, it remains completely in frames of standard diffusion approximation. The algorithms based upon the diffusion approximation would not lead to a resolution that is better than 5–10 mm. These techniques use absorption changes in tissue to determine the inverse from the transmission data inverse algorithm. The diffusion approximation is not valid at a distance smaller than 7 $l_r$, where $l_r$ is 1 to 2 mm giving 7 to 14 mm resolution. In addition, these approaches need referenced medium to compare with to determine the differences. Furthermore, the absorption in tissue in the near IR is low, absorption length $l_a \geq 50$ mm which means that mm detects will not be simply seen or detected. The absorption length $l_a$=size of entire object. Detects will not be observed using absoption changes. J. Singer and F. Grunbaum et al., *Science*, 248, 990 (1990); Grunbaum, *SPIE*, 203, 1887 (1993) proposed an approach based on simulating photon migration as a random walk on a two (three) dimensional grid of pixels (voxels). Each pixel (voxel) k is characterized by a set of parameters $\{w\}_k$ describing its absorption and scattering efficiency. The probability $P_{ij}$ for a photon launched at a pixel i on the boundary of a medium to be detected at the pixel j can be calculated. Considering $P_{ij}$ as experimental data the set $\{w\}_k$ can be restored. So far only the two-dimensional case has been numerically realized with photons allowed to wander in four or eight directions in an isotropic manner.

A linear perturbation approach was used by R. Barbour et al., *SPIE*, 192, 1437 (1991), OSA Proceeding on Advances in Optical Imaging and Photon Migration, V21, 211 (1994), in order to overcome intractable difficulties in solving the inverse problem. They assume that the absorption properties of a medium with unknown defects ($X_i$) are very close to that of a reference medium ($X_i^r$), $X_i^r$ being the absorption efficiency of the volume element i. This method depends on prior knowledge of absorption properties of the reference media and linear response function (matrix W) connecting changes in absorption properties object $\Delta X$ caused by multiple defects with changes in the array of measured signals $\Delta I$ around the object: $\Delta I = W \Delta X$. Given W and $\Delta I$ from the measurement, $\Delta X$ can be evaluated. Then X can be found. The matrix W was precalculated using the Monte Carlo approach in simulating photon migration in the reference medium. These calculations should be done for each particular shape of an object and a source-detector arrangement. So far, the simplest rectangular shape of a medium was considered and a reference turbid medium was assumed to be uniform.

Several standard numerical algorithms to minimize quadratic functionals including Tikhonov regularization approach to stabilized minimization procedure were used to find approximate solution of the linear problem $W\Delta X=\Delta I$. However, when the reference medium is very different from the test medium, the linear approximation is inaccurate which is the case in most real medical applications, say, breast and brain imaging.

There are too many shortcomings of the above methods, besides the mentioned ones: 1) they are ignoring a specific feature of biological tissues that scattered light is highly forward directed, 2) detectors are assumed to collect together photons arriving in different directions. This means that detection technique and the respective algorithms introduce additional ill-posedness to the imaging problem.

There is a need for a reconstruction method from scattered temporal data about the object which does not depend on the absorption or reference medium to compare with, which does not strictly depend on the diffusive equation, and which exploits more real physical features of the object.

SUMMARY OF THE INVENTION

It is an object of the present invention to provide a novel technique for imaging objects present in turbid media.

It is another object of the present invention to provide a technique as described above that overcomes at least some of the disadvantages associated with existing techniques for imaging objects in turbid media.

Additional objects, as well as features and advantages, of the present invention will be set forth in part in the description which follows, and in part will be obvious from the description or may be learned by practice of the invention.

The present invention is based on the present inventors'0 discovery that not all diffusive photons are equivalent in their capacity to convey information about an object located in a turbid medium and that certain diffusive photons, sometimes referred to hereinafter as "diffusive Fermat photons" or simply "Fermat photons," propagate through such media along well-defined, high-probability, curvilinear paths determined according to the principles discussed below, such paths sometimes being referred to hereinafter as "most favorable paths." Fermat photons, as contrasted with other diffusive photons, are believed by the present inventors to possess significant imaging information, and yet, are still capable of generating a relatively strong signal.

Accordingly, pursuant to the teachings of the present invention, a method of imaging an object located in a turbid medium is described herein, said method comprising the steps of: (a) illuminating the object through the turbid medium with a pulse of light, the light emergent from the turbid medium consisting of a ballistic component, a snake-like component and a diffusive component, said diffusive component including Fermat photons and non-Fermat photons; (b) gating the light emergent from the turbid medium to preferentially select Fermat photons; and (c) forming an image of the object using the gated light.

Preferably, a spatial gate is used to preferentially select Fermat photons from the light emergent from the turbid medium. This may be done by orienting the source of the illuminating light and a light detector to lie along a most favorable path travelled predominately by Fermat photons. A time gate, such as a streak camera or the like, may be used in addition to the spatial gate to more carefully select Fermat photons from the emergent light.

The above-described method may also be used to produce a tomography map or grid of a turbid medium for use in detecting an object located within the turbid medium. This may be done, for example, by providing two or more pairs of light sources and light detectors which are arranged to provide intersecting most favorable paths.

The present invention is also directed to systems constructed in accordance with the foregoing methods.

In the description which follows, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

As indicated above, the present invention is based upon the present inventors' discovery that certain diffusive photons, i.e., Fermat photons, propagate through turbid media along well-defined, high-probability, curvilinear paths referred to herein as most favorable paths (Σ's). The following discussion provides the theoretical basis for determining the most favorable paths (Σ's): First, one must consider the velocity $\vec{s}$ (l) of a photon propagating along a certain path σ as a function of the path length l traveled by the time t=l/c, where c is the speed of light in the medium. The following equation should apply at each point along the photon path:

$$\vec{s}(l)\cdot\vec{s}(l)=c^2 \qquad (1)$$

The geometric shape of the path σ (photon trajectory $\vec{r}_\sigma(l)$) can be found by integration:

$$\vec{r}_\sigma(l) = \int \vec{s}_\sigma(l)\frac{dl}{c} \qquad (2)$$

We then consider the functional space of different photon paths σ in the volume of interest. When the medium consists of scatterers possessing a strongly forward directed polar diagram, the probability P[σ] of a certain path σ is determined by the following expression:

$$P[\sigma] = \exp\left\{ -\frac{l_t}{2c^2} \int \frac{d\vec{s}}{\sigma\, dl}\, d\vec{s} \right\} \qquad (3)$$

where $l_t$ is the photon transport free path, and integration is performed along the path σ.

The most favorable path Σ then corresponds to the extremum of P[σ]:

$$\left( \frac{\delta P[\sigma]}{\delta\sigma} \right)_{\sigma=\Sigma} = 0, \qquad (4)$$

under the condition expressed in equation (1). Equations (3) and (4) may be considered a generalization of the conventional Fermat principle for the case of turbid media. The Σ-path (Fermat photon trajectory corresponding to certain initial and final coordinates and velocities) is determined by the following equation, which results from equation (4):

$$\frac{d^2}{dl^2}\vec{S}(l) - \lambda(l)\vec{S}(l) = \vec{C}, \qquad (5)$$

where $\vec{S}(l)$ is the photon velocity $\vec{s}(l)$ corresponding to the most favorable path Σ, $\vec{C}$ is arbitrary constant vector, λ(l) is the Lagrange multiplier reflecting the mutual dependence of the vector $\vec{S}(l)$ components.

Without violating generality, the 2D-solution of equations (1) and (5) can then be considered and tested experimentally since the mutual dependence of the vector $\vec{S}(l)$ components is involved in the 2D-case (3D-consideration adds little to the problem). The corresponding experimental source-detector arrangement, which may be used to observe Fermat photons, is discussed below.

Next, we introduce the components v and u of the vector $\vec{S}(l)$ in the (x,y) plane one obtains from equations (1) and (5):

$$\dot{v}-\lambda v=C_1$$
$$\dot{u}-\lambda u=C_2$$
$$v^2+u^2=c^2 \qquad (6)$$

(A dot over a symbol denotes the derivative with respect to l.)

One can then easily verify that the solution of equation (6) can be represented in the following form:

$$v = c \cdot \cos \alpha \qquad (7)$$
$$u = c \cdot \sin \alpha$$
$$\lambda = -\dot{\alpha}^2 - \frac{\delta}{2\tau^2} \sin(\alpha + \phi)$$
$$\dot{\alpha}^2 = \frac{1}{\tau^2} (\pm 1 + \delta \sin(\alpha + \phi))$$

where $\tau$, $\delta$, $\phi$ are arbitrary constants ($2C_1=c\delta\sin\phi/\tau^2$, $2C_2=c\delta\cos\phi/\tau^2$). From equations (2) and (7), it then follows that the Fermat photon paths have an exact analytic representation in the parametric form:

$$x = \tau \int_{\gamma_0}^{\gamma} \frac{\cos(\gamma-\phi)d\gamma}{(\pm 1 + \delta\sin\gamma)^{1/2}} \qquad (8)$$

$$y = \tau \int_{\gamma_0}^{\gamma} \frac{\sin(\gamma-\phi)d\gamma}{(\pm 1 + \delta\sin\gamma)^{1/2}}$$

$$l = \tau \int_{\gamma_0}^{\gamma} \frac{d\gamma}{(\pm 1 + \delta\sin\gamma)^{1/2}}$$

where $\gamma_0$ is again an arbitrary constant, and the origin of the reference frame is chosen at the starting point of the photon path. The quantity $\gamma-\gamma_0$ represents the photon velocity angle of rotation achieved by the moment it has passed the path length l along the trajectory. The parameter $\phi$ is the initial phase of the mentioned rotation. As a consequence of highly forward directed scattering, the Fermat paths do not depend much on $l_r$. Without violating the generality of solution (8), one can set $\phi=\gamma_0$ by appropriately choosing the orientation of the coordinate frame.

Solution (8) depends altogether upon 4 arbitrary constants. A particular most favorable path $\Sigma$ and the respective values of the parameters are determined by giving the total length L the path (the traveling time T=L/c), the coordinates of starting and ending points, and the starting and ending directions of the photon velocity.

Figure 1A:
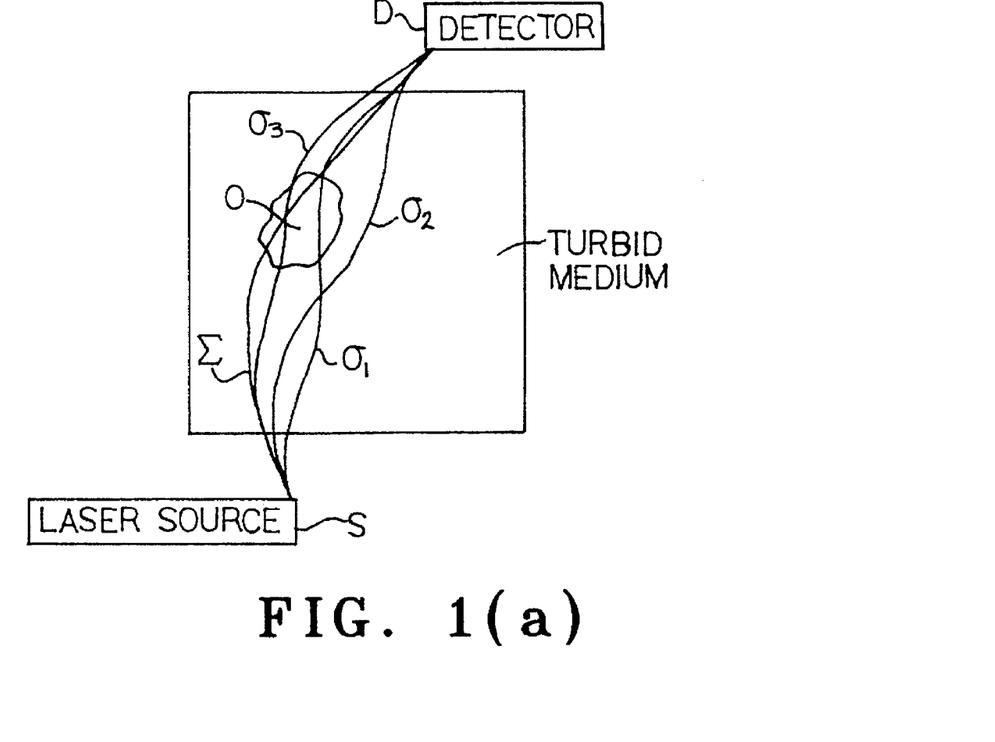
FIG. 1(a) is a schematic representation of a most favorable path Σ traveled by diffusive Fermat photons and less probable paths $\sigma_1$, $\sigma_2$ and $\sigma_3$ traveled by diffusive non-Fermat photons through a turbid medium between a source S and a detector D.
Figure 1B:
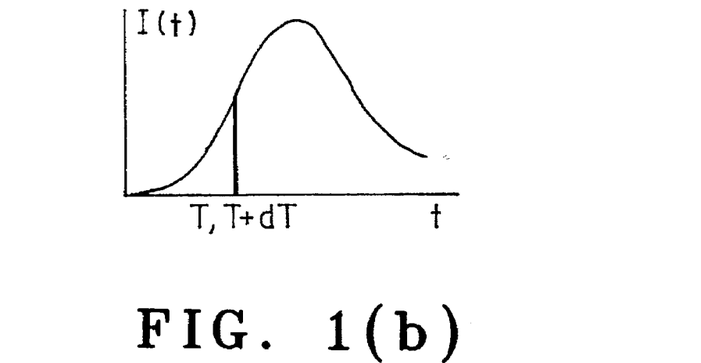
FIG. 1(b) is a graphic representation of the temporal distribution of light traversing through a turbid medium, the diffusive Fermat photons being identified by a dark band.

Referring now to FIG. 1(a), there is shown a schematic representation of a most favorable path $\Sigma$ traveled by diffusive Fermat photons and less probable paths $\sigma_1$, $\sigma_2$ and $\sigma_3$ traveled by diffusive non-Fermat photons through a turbid medium between a ultrashort laser pulse source S and a detector D. Source S and detector D are collimated to emit and to collect light, respectively, over narrow solid angles. Different photon paths a satisfying initial and final conditions contributing to the detector readings taken at the time slice T, T+dT are schematically shown in FIG. 1(b). All paths represented in FIG. 1(a) have the same length and the same tangents at source S and detector D, but the $\Sigma$-path has the greatest probability of having a photon travel thereover. Most of the photons detected by detector D travel along a narrow branch of paths concentrated around the $\Sigma$-path. When an obstacle O crosses the $\Sigma$-path, it leads to a large change in the detector readings at a given time slice T, T+dT.

Figure 2A:
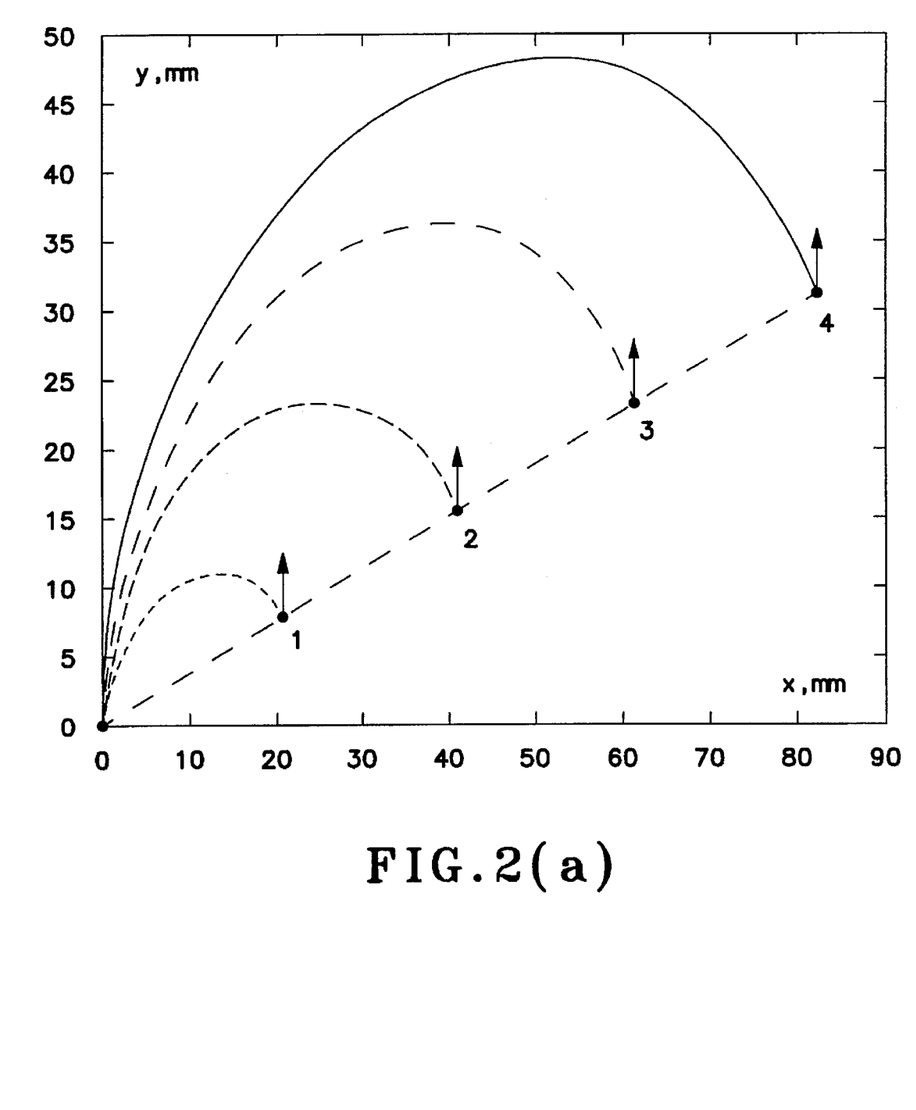
FIG. 2(a) is a graphic representation of a family of calculated self-similar Fermat paths for a light source/detector pair, the lengths of the paths being (1) 28 mm; (2) 57 mm; (3) 85 mm; and (4) 113 mm (the dashed straight line being used to connect the positions of sources and/or detectors)
Figure 2B:
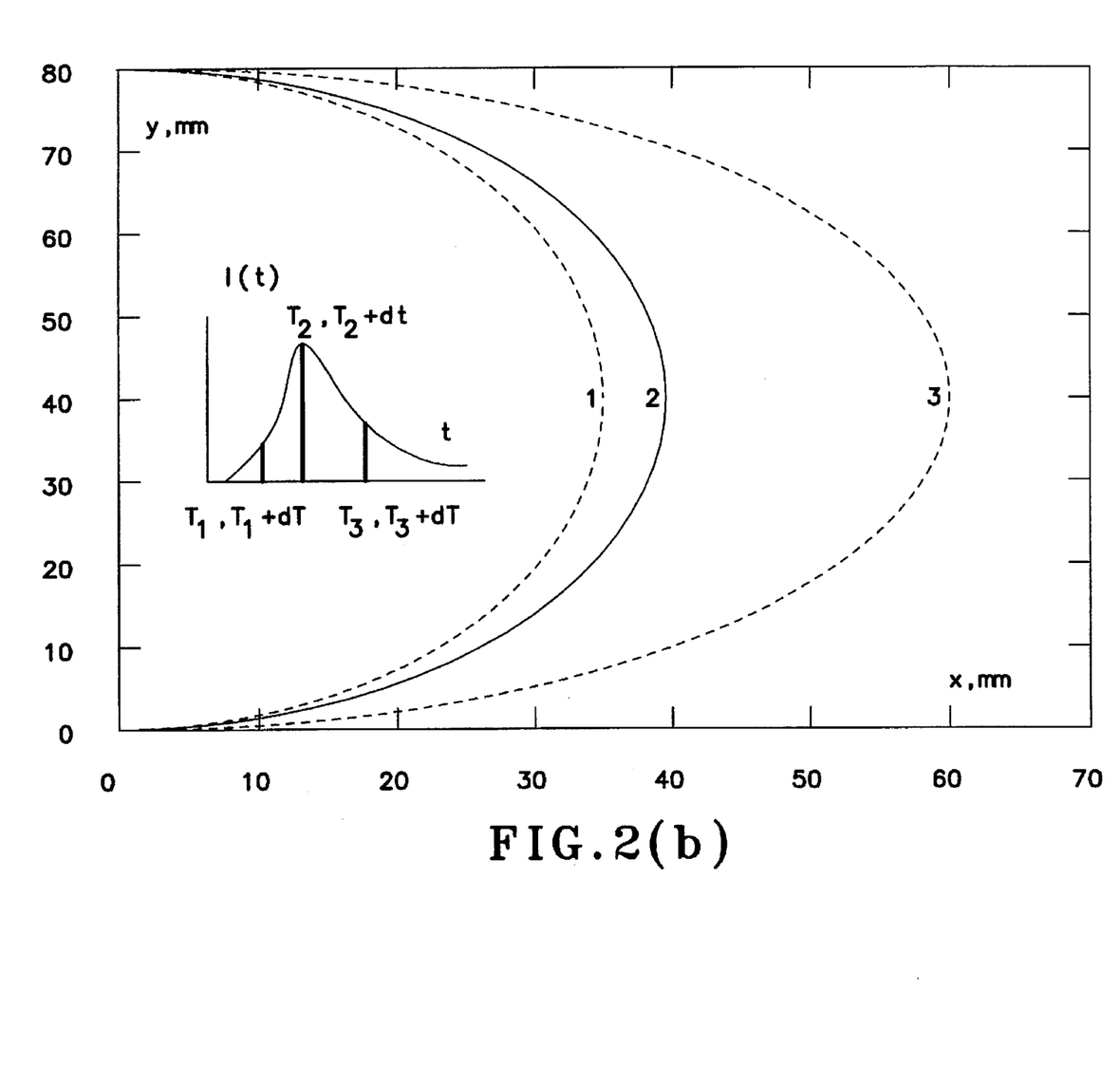
FIG. 2(b) is a graphic representation of a family of calculated self-similar Fermat paths for a second light source/detector pair, the lengths of the paths being (1) 119 mm; (2) 126 mm; and (3) 164 mm (the paths corresponding to different time slices, $T_1+dT$, $T_2+dT$, $T_3+dT$, on the same detected intensity temporal profile, which is schematically depicted in the insert)
Figure 2C:
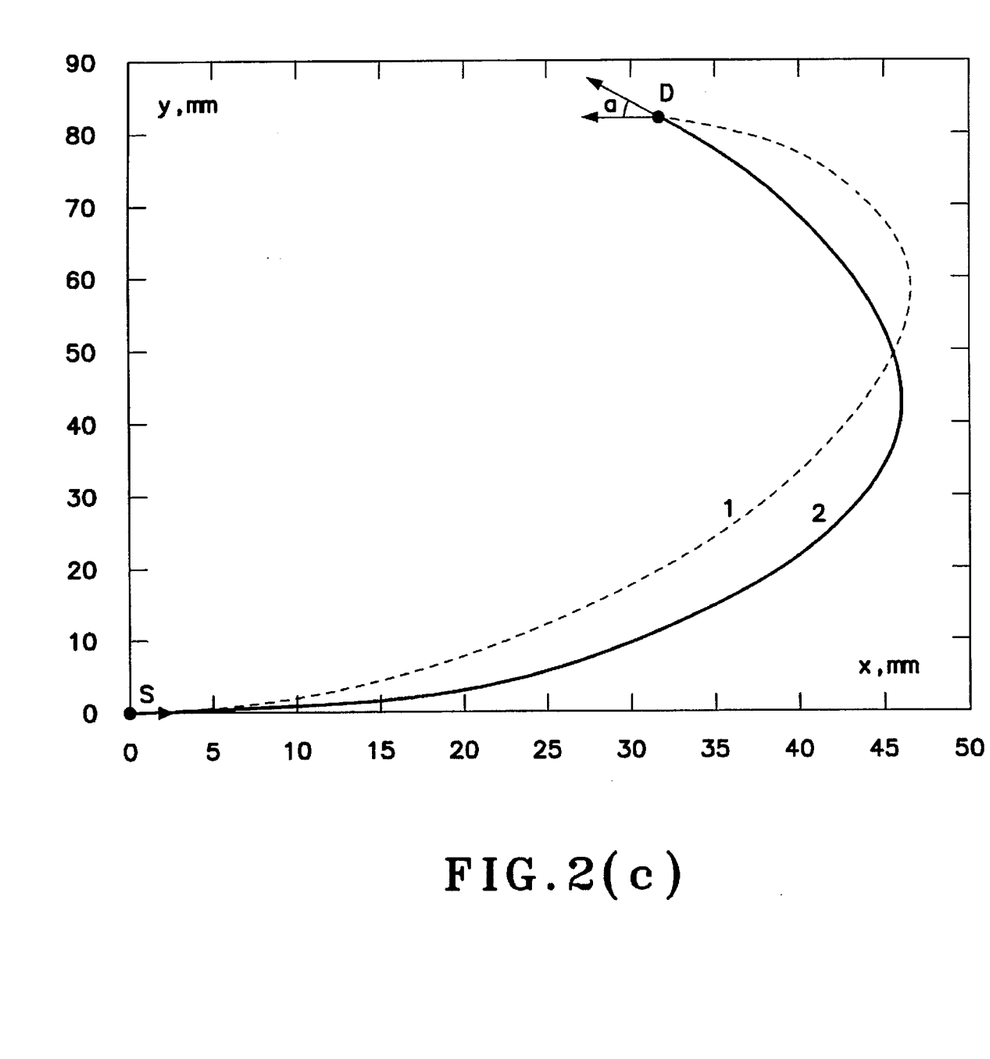
FIG. 2(c) is a graphic representation of a family of calculated self-similar Fermat paths for a second light source/detector pair and a time of detection T=500 ps, the index of refraction being taken to be 1.33 and the angles between directions of emission and detection being (1) 180 degrees; (2) 130 degrees (α=50 degrees)

It is clear from solution (8) above that $\Sigma$-paths possess self-similar properties. Given a particular $\Sigma$-path, one can generate the whole family of $\Sigma$-paths corresponding to the same source and detector orientations simply by a uniform dilatation, with the parameter $\tau$ as the modulus of dilatation. An example of such a family is shown in FIG. 2(a). The starting and ending points of each curve can be considered the source and detector positions, respectively. The orientation of the source (or detector) corresponds to the tangent at the starting (or ending) point of a path. Another example of a family of related $\Sigma$-paths is shown in FIG. 2(b), where most favorable paths differing only by their lengths are depicted for different source and detector positions. This means that, for the given source-detector configuration (positions and orientations), these $\Sigma$-paths correspond to different time slices on the same detected intensity temporal profile. A third example of a family of related $\Sigma$-paths for a given source-detector arrangement is depicted in FIG. 2(c). The only difference between the $\Sigma$-paths in FIG. 2(c) is the orientation of the detector (angle of arrival). It can be seen from FIG. 2(c) that the shape of a path pursued by a Fermat photon is sensitive to the mutual orientation of the source and detector.

Figure 3A:
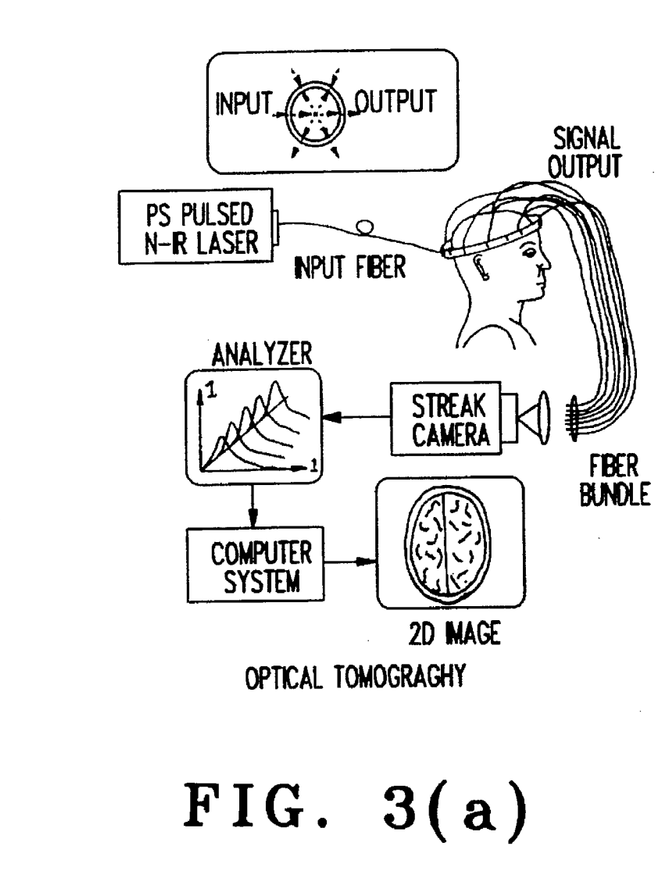
FIG. 3(a) is a schematic representation of a first embodiment of a system for detecting the presence of an object in a turbid medium, the system being constructed according to the teachings of the present invention.
Figure 3B:
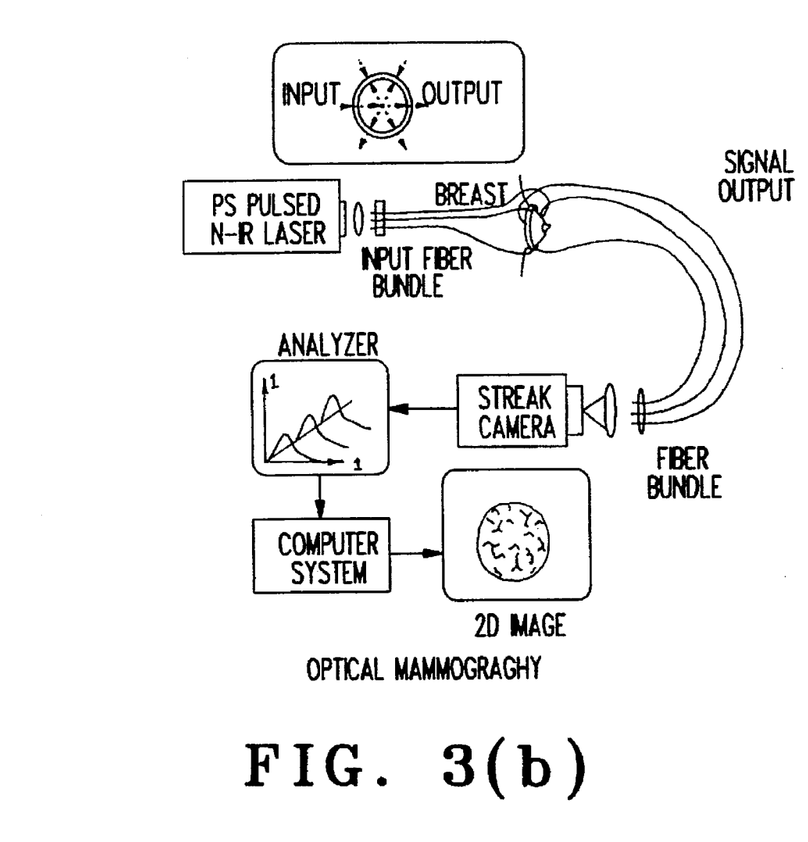
FIG. 3(b) is a schematic representation of a second embodiment of a system for detecting the presence of an object in a turbid medium, the system being constructed according to the teachings of the present invention.
Figure 4:
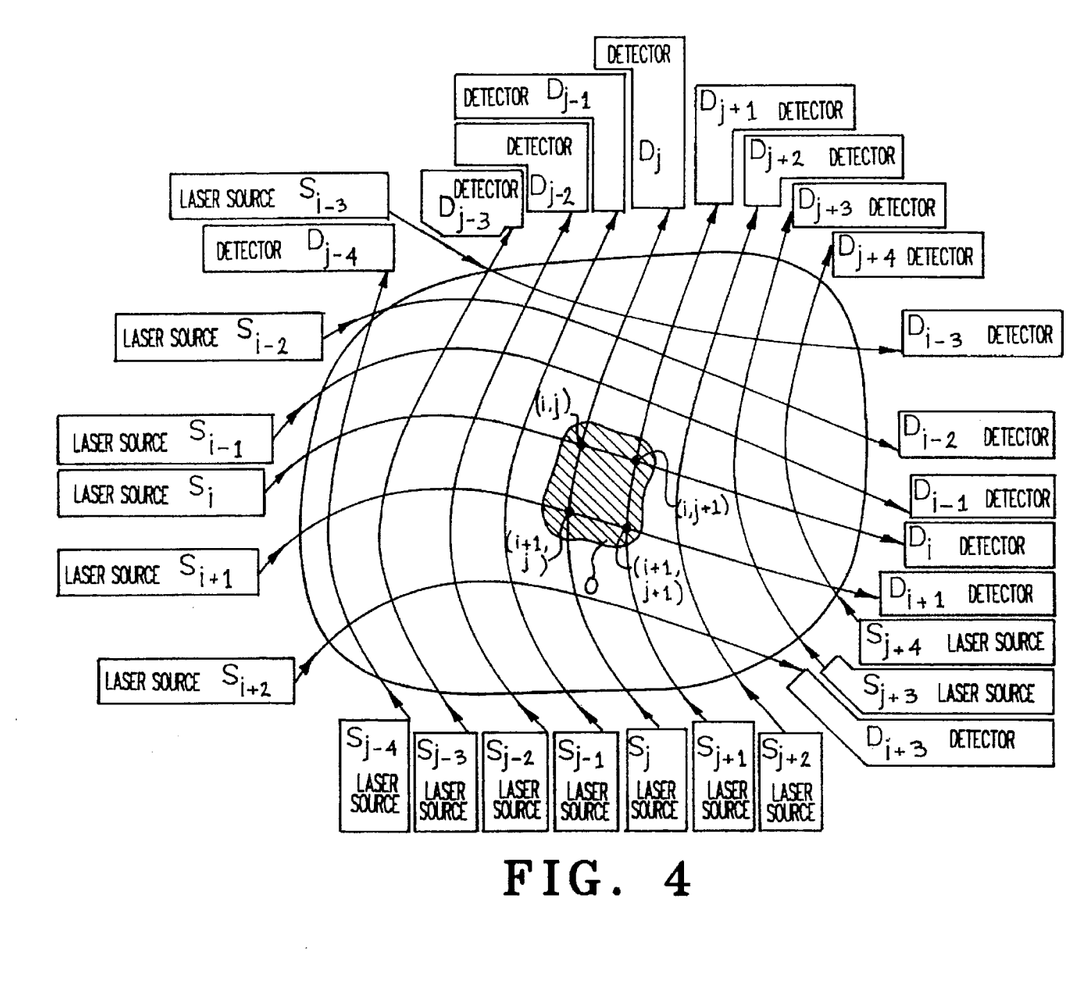
FIG. 4 is a schematic representation of the manner in which a plurality of light source/light detector pairs may be arranged in accordance with the teachings of the present invention to form a tomographic grid for use detecting the presence of an object in a turbid medium.

Using the most favorable path approach described above, one can detect an object hidden in a turbid medium, such as a biological tissue, using time-resolved optical tomography. Preferably near infrared or visible ultrashort laser pulses are used since the spectral regions from 800 to 1500 nm give the deepest penetration for biological tissues. According to the teachings of the present invention, a plurality of source-detector pairs are arranged relative to the turbid medium so that their respective most favorable paths intersect to form a grid covering the entirety of the turbid medium. The intensity time profiles are then measured at different positions and detector orientations around the turbid medium, which may be breast tissue (see FIG. 3(a)) or brain tissue (see FIG. 3(b)). FIGS. 3(a) and 3(b) show examples of possible experimental arrangements suitable for tomographic and mammographic mapping for the grid method in clinical applications of breast and brain. In these scraps one uses several input and output fibers to collect the temporal profiles around the bodies. The fiber bundles are designed to collect narrow angular spread—well collimated to about a couple of degrees or less, $\theta \leq 3°$. The signals are detected by means of a time-resolved instrument with a time response of less than 250 ps, preferably <30 ps. Such time-resolved equipment includes a streak camera, a gated photodetector, a gated image intensifier with CCD nonlinear optic SHG gate, an optical Kerr gate, and an electrooptic gate. The signals from the fiber array around the object are correlated in space and time windows. These signals are analyzed and compared for the grid matrix array to acquire a map inside the object. The main components of the instrument are pulsed light source (ps or fs mode-locked lasers), many input and output collimated fiber arrays, time resolved detector (streak camera, gated photodetector) with computer with grid analysis software. Viewed individually, each of the detectors provides some information about the position and properties of an object hidden in the turbid medium. Taken together, the detectors can be used to map the object. As an illustration of the above-described principles, a schematic 2-D example of a map of an object hidden inside a turbid medium is shown in FIG. 4. Each coordinate line represents a most favorable path between a source-detector pair (the sources and detectors being represented by arrowheads).

Thus, each intersecting point (grid node) is identified by a pair of integers (i,j). The absorbing foreign object O covers a group of grid nodes—(i,j), (i+1, j), (i, j+1) and (i+1, j+1). This would result in the simultaneous perturbation of photon propagation along coordinate lines i, i+1, j, j+1, thereby leading to a change in the photon intensities measured by the detectors along lines i, i+1, j, j+i.

Figure 5A:
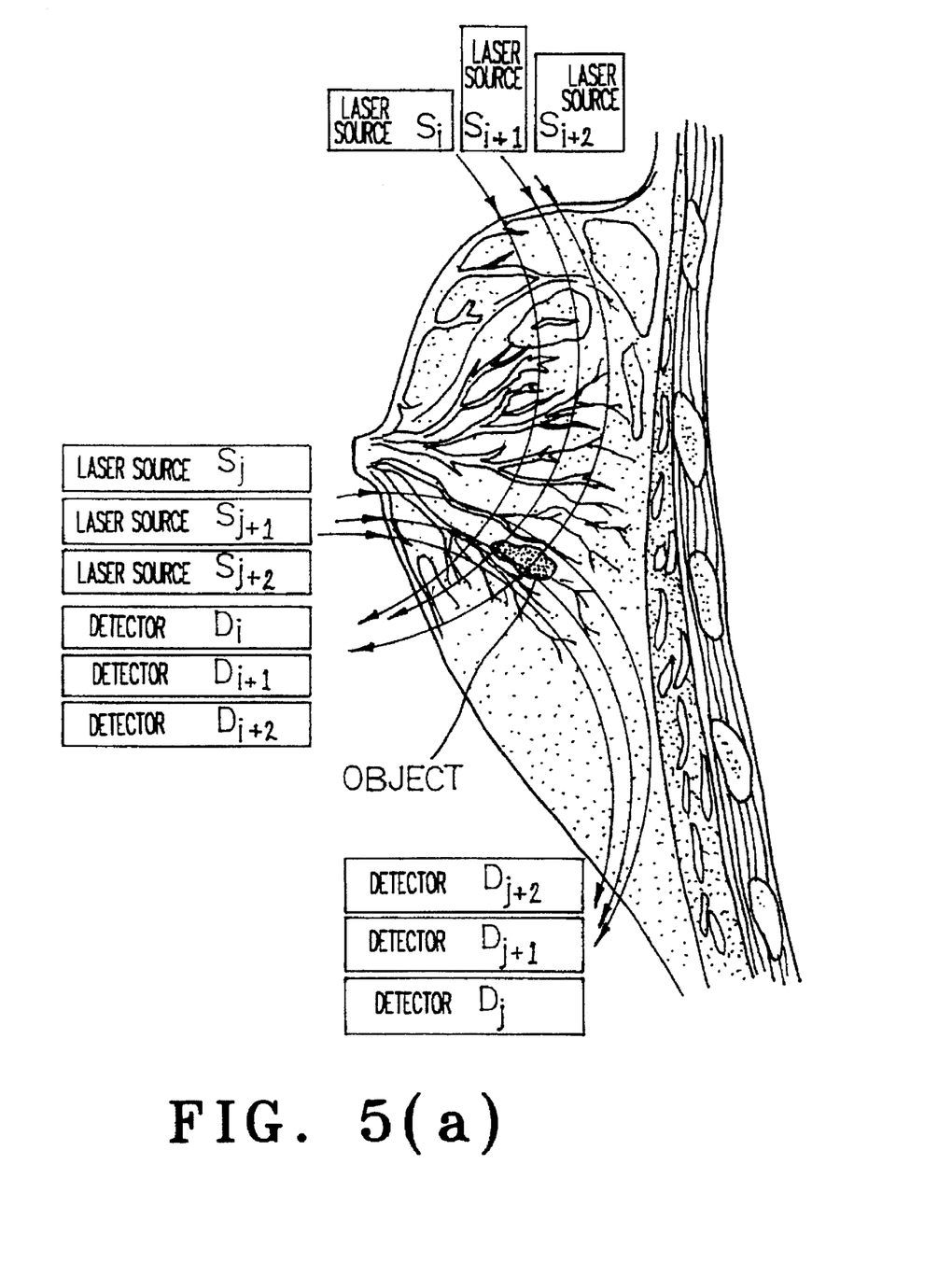
FIGS. 5(a) and 5(b) are schematic representations of the use of tomographic grids of the type illustrated in FIG. 4 for use in detecting the presence of tumors in the breast and the brain, respectively.
Figure 5B:
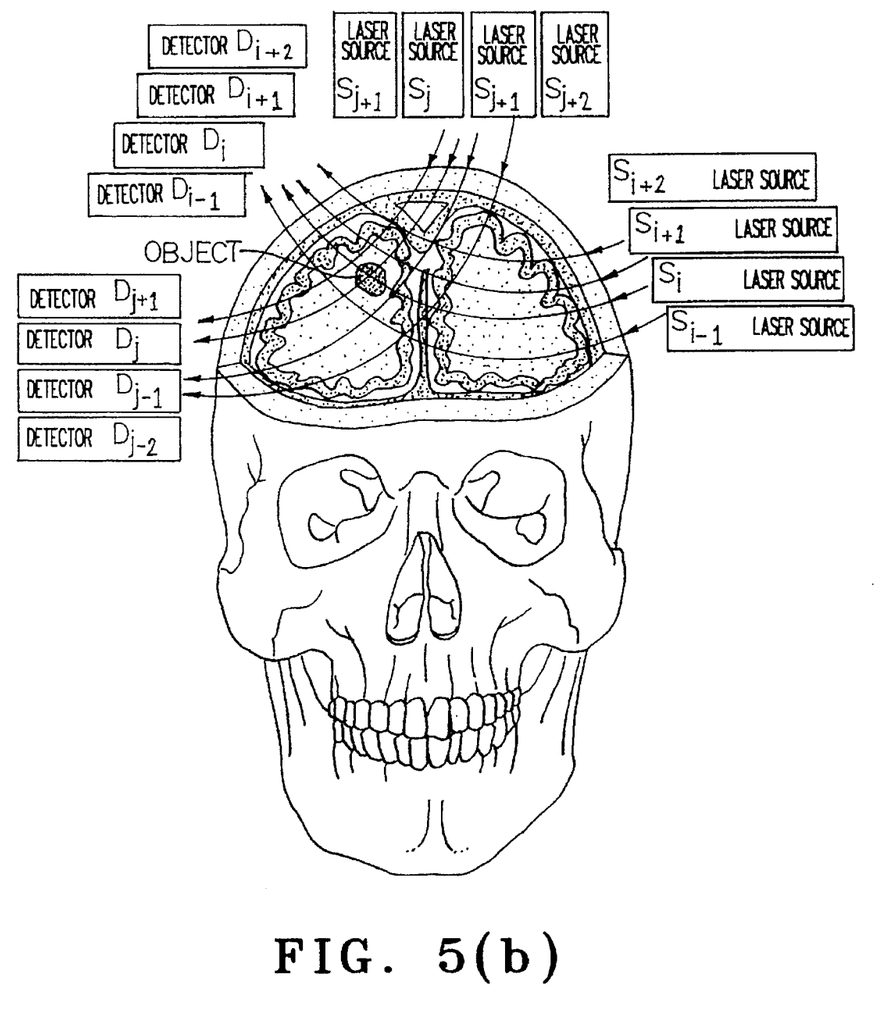

Referring to FIGS. 5(a) and 5(b), the aforementioned principles can be applied to the detection of tumors in the breast and the brain, respectively.

One important question which remains regarding the above-described technique is the resolution accuracy, which depends on the effective width $w_r$ of the branch of paths concentrated around a most favorable path. In view of the exponential dependence of the paths upon transport scattering length $l_t$, one can expect $w_r \sim l_t$, which allows a resolution of 1 mm or less for biological tissues.

Photon migration in turbid media can be described as a random walk on a spherical surface of the radius C, non-Euclidean velocity space. For a medium possessing a highly forward directed scattering the mean-square value of the deflection angle in a single collision event, is given by $\{\Delta^2\} \approx 2(1-\{\cos(\Delta)\}) \ll 1$. After each collision the photon undergoes a small velocity change step $\Delta s = c\sqrt{\{\Delta^2\}}$ in a random direction on a small almost flat spherical segment. Given the photon collision frequency $1/\tau$ the photon random walk in the velocity space is simply diffusion-like with an effective diffusion coefficient $\Delta s^2/4\tau = c^2\{\Delta^2\}/4\tau = c^3/2l_t$, where $l_t$ is the photon transport mean free path. Consider a small "volume" $d\omega = d^3r \cdot d^2s$ around the point $(\vec{r}, \vec{s})$ in 5D photon phase space ($d^3r$ stands for a spatial volume element and $d^2s$ for a spherical surface element). The photons can leave this "volume" for two reasons: due to ballistic motion and because of a change in photon velocity due to collisions described by the diffusion on the velocity sphere.

Given the above analysis it is straightforward to find the transport equation for the photon distribution function $n(t, \vec{r}, \vec{s}, \vec{s}_0)$ accounting for scattering and absorption:

$$\frac{\partial n}{\partial t} + \vec{s}\vec{\nabla}_r n - \frac{c^3}{2l_t} \Delta_s n + v_a n = \delta(t)\delta(\vec{r})\delta(\vec{s}-\vec{s}_o), \qquad (9)$$

where $\Delta_s$ stands for the Laplace operator on the velocity sphere and $v_a$ is the absorption collision frequency. The r.h.s. of Equation (9) implies initial conditions $n(t=0)=\delta(\vec{r})\delta(\vec{s}-\vec{s}_0)$ which means that initially all photons are concentrated at the origin of the coordinate frame and possess the same velocity $\vec{s}_0$ (a simulation of an incident light beam). Equation (9) reminds one of a diffusion equation, however, it is entirely different from the conventional one. First, the diffusion involved in Equation (9) occurs on the velocity sphere, rather than in real coordinate space. Second, Equation (9) describes ballistic motion which is obviously not covered by standard spatial diffusion model. Equation (9) is valid for a nonuniform turbid media with spatially varying scattering and absorption characteristics $l_t$ and $v_a$.

The solution of Equation (9) can be presented in the form of a path integral:

$$n(t,\vec{r},\vec{s},\vec{s}_0) = \int \prod_\tau d\vec{s}(\tau) \delta\left(\vec{r} - \int_0^t \vec{s}(t')dt'\right) P[\vec{s}(\tau)]. \qquad (10)$$

The functional $P[\vec{s}(t)]$ is represented by Equation (3) describing probability of each path $\sigma$ given by the function $\vec{s}(t)$, the variables t and l are related by the linear transformation $l=ct$. The $\delta$-function in Equation (10) corresponds to the fact that only paths connecting a source placed at the origin and a dector situated at the point $\vec{r}$ are to be taken into account.

Figure 6:
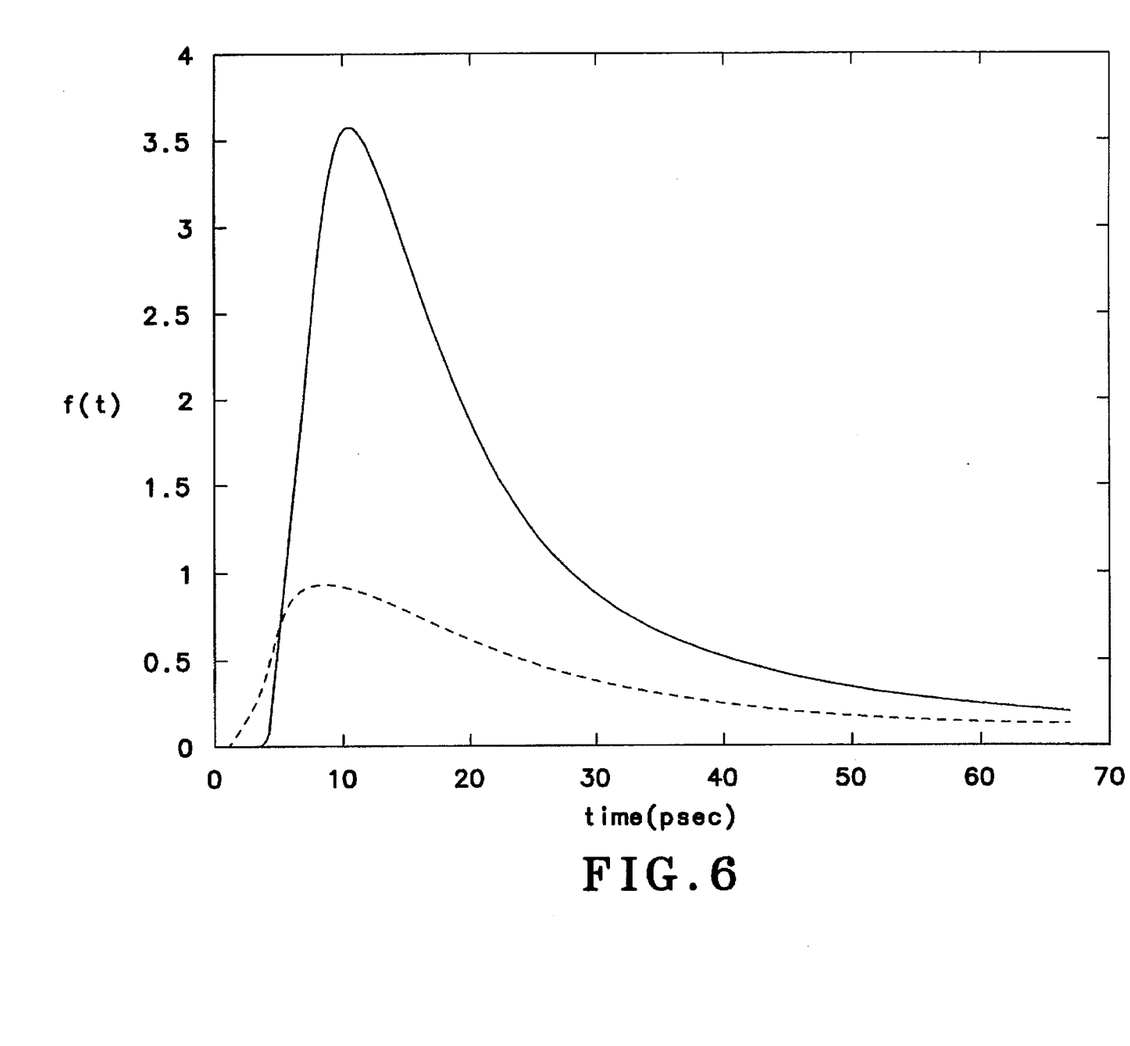
FIG. 6 is a graphic representation of the time profiles for light intensity (photon number density) f(t) at a distance L=2$l_t$ between a point-like instantaneous source and a detector. The solid line represents the solution of Equation (9); the dashed line represents standard diffusion model. 100 photons are launched at the origin of the coordinate frame in the source direction. Typical values for the biological tissues as of the photon transport free path $l_t$ and the index of refraction of the medium are assumed to be 1 mm and 1.33 mm, respectively.

Equation (9) constitutes a basis for future optical tomography and imaging algorithms with principally higher resolution than diffusion-model-based algorithms, since the former takes ballistic motion into account and describes the transition from the ballistic propagation regime to the diffusion-like behavior. To demonstrate these advantages, the results of approximate analytical calculations of the photon number density averaged over all velocity directions $$f(t,\vec{r},\vec{s}_0) = \int_{s_2} d\vec{s}\, n(t,\vec{r},\vec{s},\vec{s}_0) \qquad (11)$$

are given in FIG. 6 depicting the temporal profiles of an ultrashort laser pulse propagating in an infinite turbid medium as described by Equation (9). The results of the standard diffusion model are also presented for comparison.

FIG. 6 demonstrates that the approximate analytic solution of Equation (9) describes causality constraints: one sees an appreciable pulse arriving time delay with respect to the predictions of the diffusion theory. FIG. 6 shows that the peak of the signal detected at the distances in the longitudinal direction from the source as large as several lt is much higher than that one predicted by the standard diffusion model. Our calculations have shown that even at distances $L \sim 15 l_t$, the photons still "keep in memory" their initial velocity direction, though the two curves are rather close, which means that the diffusion-like regime is already almost attained. On the Y–Z plane (perpendicular to the initial photon's velocity) the diffusion-like regime is attained at smaller distances, $L \sim 5 l_t$.

The above analysis shows that the diffusion approximation used for imaging in biological tissues would not lead to resolution better than $5l_t$ (that is about 5–10 mm), even if technical difficulties associated with the inverse problem solution were overcome. Equation (1) as a basis of future imaging algorithms aimed at future optical tomography medical applications will lead to a resolution of the order of $l_t \sim 1$ mm.

The following observations may be made about the present invention:

(1) Fermat photons are diffusive photons traveling along well-defined, high probability paths in narrow time windows for turbid media.

(2) Fermat photons travel along favorable paths in turbid media analogous to photon propagation in transparent media by traveling the shortest optical paths.

(3) The Fermat photon paths depend upon source and detector location, orientation, position, collimation and time window for turbid media.

(4) The path trajectories for Fermat photons are obtained by the extremum of $P[\sigma]$ (given by equation (3) above) for certain source and detector location, orientation, position, collimation and time window for turbid media.

(5) The $\Sigma$-photon paths inside the media are used to locate an object in turbid media, for instance, a tumor in a breast by measuring intensities for different source and detector locations, orientations, positions, collimations and time windows. An observable grid can be formed by a set of intersecting most favorable paths (like coordinate lines on a map) covering the whole medium, by varying the source and detector positions, orientations, collimation and time slices. One can figure out regions of the grid covered by an object (e.g., a tumor) since the measured intensities depend upon path shape and the scattering and absorption along the paths.

The reconstructed map forms an image inside the medium (e.g., the breast, the brain, the prostate, the neck, etc.).

(6) Each most favorable path $\Sigma$ is uniquely determined by (a) coordinates of start $(x_0,y_0,z_0)$ and end $(x_T,y_T,z_T)$ points; (b) start and end photon velocities determined by vectors $\vec{S}_0, \vec{S}_T$, respectively, and (c) total length of a path L (or travel time T=L/c wherein c is the speed of light).

(7) Let an ultrashort light pulse source be placed at a point $(x_0,y_0,z_0)$ and let the source launch photons in the $\vec{S}_0$ direction. Let a light detector be placed at a point $(x_T,y_T,z_T)$ and let it collect photons arriving at $\vec{S}_T$ direction at a narrow time slice (T,T+dT). A majority of photons launched by the source and detected by the detector travel along most favorable paths $\Sigma$.

(8) If points $(x_0,y_0,z_0)$ and $(x_T,y_T,z_T)$ and vectors $\vec{S}_0$ and $\vec{S}_T$ lay in a certain plane, then the corresponding $\Sigma$-paths lay in the same plane.

(9) Near infrared wavelengths (800 nm to 1500 nm) may advantageously be used to highlight the tumor scattering properties from fat, glandular and water content in a breast. The molecular content and structure of cancer tissues are different from that of normal tissues.

(10) Near infrared wavelengths may be used to determine whether a tumor is cancerous or benign based on scattering differences between the tumor in the 800 nm, 1060 nm and 1250 nm regions for fat, glandular and water content.

(11) Picosecond and femtosecond Ti:Sapphire lasers, Forsterite lasers and/or Cr:YAG lasers may be used in combination to form $\Sigma$-paths grid maps to determine if the tissue or tumor is cancerous or benign using various source and detector angular positions and time windows.

(12) A streak camera and mode-locked laser with fiber bundles for input and output locations around the breast to determine a $\Sigma$-map image of the turbid object, e.g., map of the breast, tumor in the breast, prostate, brain, etc.

(13) One could change the near infrared wavelengths and tune wavelengths to highlight $\Sigma$-reconstructed image map of breast or other tissue in 2D and 3D.

(14) An imaging system for use in practicing the present invention could comprise an ultrafast laser source; picosecond temporal measurement detectors; space, angle and time gates; and fibers to measure source-detector intensities around the object forming an intersecting grid. The spatial location $(x_i,y_i,z_i)$, orientation $(\theta_i,\phi_i)$ and collection angle, $\alpha$, of the optical fiber bundles around the body are critical to locate the $\Sigma_j$ path for grid analysis. One needs to collect well-defined scattered signals in time on a narrow cone using either collimated fibers or fibers which restricted the collection angle and orientation of the scattered signals. Several companies can produce such fibers—Meteor Optics, Inc. CIT or SELFOC fiber collimator by NSG American, Inc. to achieve acceptance angle of as small as 1° to 3° which is necessary to achieve ≦1 mm resolution in mapping an object.

Given the equations for $\Sigma$ (Eq. 6), one can approximate the ideal favorable path using circles or ellipse photon paths between the observation and source points in the analysis of the grid map.

(15) Equation (9) is an equation describing nonsteady photon transport in highly forward scattering turbid media of the type of biological and medical tissues.

(16) Equation (9) describes photon ballistic motion together with scattering and absorption events.

(17) The scattering events are described by Equation (9) as "diffusion" on the velocity sphere, rather than in coordinate space.

(18) Equation (9) is valid for nonuniform turbid media with the mean photon free path $l_t$ and the absorption coefficient $v_a$ varying in space.

(19) Equation (9) is a basis for calculating the evolution of ultrashort laser pulses in turbid media, particularly, intensity temporal profiles measured in time-resolved experiments described herein.

(20) Equation (9) is used in an inverse algorithm for imaging to give a map of the internal structure of the object, i.e., breast and brain to detect tumor.

(21) Equation (9) is used in the grid method using different time windows.

(22) Equation (9) underlies future mathematical algorithms in the field of optical tomography and imaging for highly forward scattering media such as biological and medical tissues.

(23) Solution of Equation (9), i.e., Equation (11) is used in items #15 to 22 around the object to be measured to form an image using $\Delta t$ windows data of f(t).

(24) Solution of Equation (9), i.e., Equation (11) is used for sources and detectors in a grid map about object to reconstruct a map of internal structure of the object.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of imaging an object located in a turbid medium, said method comprising the steps of:
   (a) illuminating the object through the turbid medium with a pulse of light, whereby light emerges from the turbid medium, the emergent light from the turbid medium consisting of a ballistic component, a snake-like component and a diffusive component, said diffusive component including Fermat photons and non-Fermat photons;
   (b) gating the emergent light from the turbid medium to preferentially select Fermat photons; and
   (c) forming an image of the object using the gated light.

2. The method as claimed in claim 1 wherein said gating step comprises spatially gating the emergent light from the turbid medium.

3. The method as claimed in claim 2 wherein said spatially gating step comprises emitting said pulse of light from a collimated source and positioning a collimated light detector along a most favorable path traveled by Fermat photons.

4. The method as claimed in claim 1 wherein said gating step comprises temporally gating and spatially gating the emergent light from the turbid medium.

5. The method as claimed in claim 4 wherein said spatially gating step comprises emitting said pulse of light from a collimated source and positioning a collimated light detector along a most favorable path traveled by Fermat photons.

6. The method as claimed in claim 5 wherein said temporally gating step comprises temporally resolving the light detected by said collimated light detector.

7. The method as claimed in claim 6 wherein said temporally gating step is performed using a streak camera.

8. The method as claimed in claim 1 wherein said pulse of light has a wavelength of about 800 nm to about 1500 nm.

9. The method as claimed in claim 1 wherein said pulse of light is an ultrashort pulse of light.

10. The method as claimed in claim 9 wherein said pulse of light is emitted from a laser selected from the group consisting of picosecond and femtosecond Ti:Sapphire lasers, Forsterite lasers and Cr:YAG lasers.

11. The method as claimed in claim 1 wherein said turbid medium is a biological tissue.

12. The method as claimed in claim 11 wherein said biological tissue is selected from the group consisting of human breast tissue, human brain tissue, human neck tissue and human prostate tissue and wherein said object is a tumor.

13. A system for imaging an object located in a turbid medium, said system comprising:
   (a) means for illuminating the object through the turbid medium with a pulse of light, whereby light emerges from the turbid medium, the emergent light consisting of a ballistic component, a snake-like component and a diffusive component, said diffusive component including Fermat photons and non-Fermat photons;
   (b) means for gating the emergent light from the turbid medium to preferentially select Fermat photons; and
   (c) means for forming an image of the object using the gated light.

14. The system as claimed in claim 13 wherein said gating means comprises spatial gating means and temporal gating means.

15. The system as claimed in claim 14 wherein said spatial gating means comprises a collimated light detector positioned along a most favorable path traveled by Fermat photons, said collimated light detector having an output.

16. The system as claimed in claim 15 wherein said temporal gating means comprises a streak camera coupled to the output of said collimated light detector.

17. A method of generating a tomographic map of a turbid medium, said method comprising the steps of:
   (a) illuminating the turbid medium with a first pulse of light, whereby light emerges from the turbid medium, the emergent light from the turbid medium consisting of a ballistic component, a snake component and a diffusive component, the diffusive component comprising Fermat photons and non-Fermat photons, at least some of the Fermat photons having traveled through the turbid medium along a first most favorable path;
   (b) illuminating the turbid medium with a second pulse of light, whereby light emerges from the turbid medium, the emergent light from the turbid medium consisting of a ballistic component, a snake component and a diffusive component, the diffusive component comprising Fermat photons and non-Fermat photons, at least some of the Fermat photons having traveled through the turbid medium along a second most favorable path, said first most favorable path and said second most favorable path intersecting at a point within the turbid medium;
   (c) gating the emergent light from the turbid medium attributable to said first pulse of light so as to preferentially select therefrom Fermat photons;
   (d) gating the emergent light from the turbid medium attributable to said second pulse of light so as to preferentially select therefrom Fermat photons; and
   (e) using the photons gated in steps (c) and (d) to generate a tomographic map of the turbid medium.

18. The method as claimed in claim 17 wherein said gating step of step (c) comprises positioning a collimated light detector to detect light traveling along said first most favorable path and wherein said gating step of step (d) comprises positioning a collimated light detector to detect light traveling along said second most favorable path.

19. The method as claimed in claim 18 wherein said gating step of step (c) further comprises temporally resolving the light detected by said collimated light detector to preferentially select Fermat photons and wherein said gating step of step (d) further comprises temporally resolving the light detected by said collimated light detector to preferentially select Fermat photons.

20. The method as claimed in claim 17 further comprising the steps of illuminating the turbid medium with one or more additional pulses of light, each of said additional pulses of light including Fermat photons which travel through the turbid medium along a most favorable path which intersects at least one of said first most favorable path and said second most favorable path within the turbid medium; gating the emergent light from the turbid medium attributable to each of said additional pulses of light so as to preferentially select therefrom Fermat photons; and using the gated Fermat photons from said additional pulses of light, together with the gated Fermat photons from steps (c) and (d), to generate a tomographic map of the turbid medium.

21. The method as claimed in claim 17 wherein each of said first and said second pulses of light has a wavelength of about 800 nm to about 1500 nm.

22. The method as claimed in claim 17 wherein each of said first and said second pulses of light is an ultrashort pulse of light.

23. The method as claimed in claim 22 wherein each of said first and said second pulses of light is emitted from a laser selected from the group consisting of picosecond and femtosecond Ti:Sapphire lasers, Forsterite lasers and Cr:YAG lasers.

24. The method as claimed in claim 17 wherein said turbid medium is a biological tissue.

25. The method as claimed in claim 24 wherein said biological tissue is selected from the group consisting of human breast tissue, human brain tissue, human neck tissue and human prostate tissue and wherein said object is a tumor.

26. A system for generating a tomographic map of a turbid medium, said system comprising:
   (a) means for illuminating the turbid medium with a first pulse of light, whereby light emerges from the turbid medium, the emergent light from the turbid medium consists of a ballistic component, a snake component and a diffusive component, the diffusive component comprising Fermat photons and non-Fermat photons, at least some of the Fermat photons having traveled through the turbid medium along a first most favorable path;
   (b) means for illuminating the turbid medium with a second pulse of light, whereby light emerges from the turbid medium, the emergent light from the turbid medium consists of a ballistic component, a snake component and a diffusive component, the diffusive component comprising Fermat photons and non-Fermat photons, at least some of the Fermat photons having traveled through the turbid medium along a second most favorable path, said first most favorable path and said second most favorable path intersecting at a point within turbid medium;
   (c) means for gating the emergent light from the turbid medium attributable to said first pulse of light so as to preferentially select therefrom Fermat photons;
   (d) means for gating the emergent light from the turbid medium attributable to said second pulse of light so as to preferentially select therefrom Fermat photons; and
   (e) means for generating a tomographic map of the turbid medium using the Fermat photons detected in steps (c) and (d).

* * * * *